United States Patent
Vogelaar et al.

(10) Patent No.: US 9,637,757 B2
(45) Date of Patent: May 2, 2017

(54) PEPINO MOSAIC VIRUS RESISTANT TOMATO PLANT

(71) Applicant: RIJK ZWAAN ZAADTEELT EN ZAADHANDEL B.V., De Lier (NL)

(72) Inventors: Arie Vogelaar, De Lier (NL); Evert Willem Gutteling, De Lier (NL); Dorthe Bettina Drager, De Lier (NL); Rudolf Verhoef, De Lier (NL); Zeger Otto Van Herwijnen, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 396 days.

(21) Appl. No.: 13/774,665

(22) Filed: Feb. 22, 2013

(65) Prior Publication Data

US 2013/0254928 A1    Sep. 26, 2013

Related U.S. Application Data

(63) Continuation-in-part of application No. PCT/EP2012/071733, filed on Nov. 2, 2012.

(30) Foreign Application Priority Data

Nov. 2, 2011   (EP) .................................... 11187454
Feb. 13, 2012  (EP) .................................... 12155235
Oct. 12, 2012  (EP) .................................... 12188367

(51) Int. Cl.
```
A01H 5/08      (2006.01)
A01H 1/00      (2006.01)
C12N 15/82     (2006.01)
A01H 1/04      (2006.01)
C12N 15/00     (2006.01)
```
(52) U.S. Cl.
CPC ........... *C12N 15/8283* (2013.01); *A01H 1/04* (2013.01); *A01H 5/08* (2013.01)

(58) Field of Classification Search
None
See application file for complete search history.

(56) References Cited

PUBLICATIONS

"TSA: Physalis peruviana Php00a01887.09333 mRNA sequence", Database DDBJ/EMBL/GenBank, Accession No. JO133425, Jul. 27, 2011, uploaded: http://www.ncbi.nlm.nih.gov/nuccore/340825349.

Lanzhuang, et al. "Efficient hybridization between Lycopersicon esculentum and L. peruvianum via 'embryo rescue' and in vitro propagation" Plant Breeding, 1996, 115:251-256.

Pico, et al. "Widening the genetic basis of virus resistance in tomato" Scientia Horticulturae, 2002, 94:73-89.

Ling, et al. "Sources of Resistance to Pepino mosaic virus in Tomato Accessions" Plant Disease, 2007, 91(6):749-753.

Soler-Aleixandre, et al. "Sources of Resistance to Pepino mosaic virus (PepMV) in Tomato" HortScience, 2007, 42(1):40-45.

54826.1 After-Cooking Darkening C. Solanum tuberosum cDNA clone 54826 5', mRNA sequence, Database DDBJ/EMBL/GenBank and Accession No. CP002666, Oct. 2005, uploaded: http://www.ncbi.nlm.nih.gov/nucest/52826084.

64384.1 Mixed Leaf Solanum tuberosum cDNA clone 64384 5', mRNA sequence, Database DDBJ/EMBL/GenBank and Accession No. CV499975, Oct. 2005, uploaded: http://www.ncbi.nlm.nih.gov/nucest/53782332.

40936.3 Cold Sweetening B Solanum tuberosum cDNA clone 40936 3', mRNA sequence, Database DDBJ/EMBL/GenBank and Accession No. DN922131, Oct. 2005, uploaded: http://www.ncbi.nlm.nih.go/nucest/62908464.

S_T3_226_G03_Apr. 20, 2006_019.1 LIPTS Solanum tuberosum cDNA clone S_T3_226_G03_Apr. 20, 2006_019, mRNA sequence, Database DDBJ/EMBL/GenBank and Accession No. JG700002, Mar. 2011, uploaded: http://www.ncbi.nlm.nih.gov/nucest/326771421.

Notification of Reasons for Refusal dated Jul. 28, 2016, which issued during prosecution of Japanese Application No. 2014-539344.

*Primary Examiner* — Phuong Bui
(74) *Attorney, Agent, or Firm* — Vedder Price P.C.; Thomas J. Kowalski; Deborah L. Lu

(57) ABSTRACT

The present invention relates to a tomato plant (*Solanum lycopersicum* L.) which may comprise a genetic determinant that confers resistance to Pepino Mosaic Virus (PepMV), wherein the resistance is characterized by the presence of at least QTL1 and/or QTL2. The invention also relates to sources for obtaining said genetic determinant, representative seed of which were deposited with the NCIMB under accession numbers NCIMB 41927, NCIMB 41928, NCIMB 42068, and NCIMB 42069. The invention further relates to seeds and progeny of the plant and to its fruits and processed fruits. In addition the invention relates to molecular markers linked to PepMV resistance conferring QTLs and the use thereof.

14 Claims, No Drawings

SEQUENCE LISTING

```
<160> NUMBER OF SEQ ID NOS: 9

<210> SEQ ID NO 1
<211> LENGTH: 31
<212> TYPE: DNA
<213> ORGANISM: Solanum lycopersicum
<220> FEATURE:
<221> NAME/KEY: source
<222> LOCATION: 1..31
<223> OTHER INFORMATION: /mol_type="DNA"
      /organism="Solanum lycopersicum"

<400> SEQUENCE: 1
gatgatcccc caatggtcaa gaaatcttgc a                                 31

<210> SEQ ID NO 2
<211> LENGTH: 31
<212> TYPE: DNA
<213> ORGANISM: Solanum lycopersicum
<220> FEATURE:
<221> NAME/KEY: source
<222> LOCATION: 1..31
<223> OTHER INFORMATION: /mol_type="DNA"
      /organism="Solanum lycopersicum"

<400> SEQUENCE: 2
cactggtgaa aaagtggcaa ttaaaaaaat t                                 31

<210> SEQ ID NO 3
<211> LENGTH: 31
<212> TYPE: DNA
<213> ORGANISM: Solanum lycopersicum
<220> FEATURE:
<221> NAME/KEY: source
<222> LOCATION: 1..31
<223> OTHER INFORMATION: /mol_type="DNA"
      /organism="Solanum lycopersicum"

<400> SEQUENCE: 3
ctctcaagtt ccagataccg cttctgaggg a                                 31

<210> SEQ ID NO 4
<211> LENGTH: 31
<212> TYPE: DNA
<213> ORGANISM: Solanum lycopersicum
<220> FEATURE:
<221> NAME/KEY: source
```

```
<222> LOCATION: 1..31
<223> OTHER INFORMATION: /mol_type="DNA"
      /organism="Solanum lycopersicum"

<400> SEQUENCE: 4
tctcgttcgt gttctcgtct cctctaatct c                              31

<210> SEQ ID NO 5
<211> LENGTH: 31
<212> TYPE: DNA
<213> ORGANISM: Solanum lycopersicum
<220> FEATURE:
<221> NAME/KEY: source
<222> LOCATION: 1..31
<223> OTHER INFORMATION: /mol_type="DNA"
      /organism="Solanum lycopersicum"

<400> SEQUENCE: 5
ggacattgag cagatttctt actggcttct g                              31

<210> SEQ ID NO 6
<211> LENGTH: 31
<212> TYPE: DNA
<213> ORGANISM: Solanum lycopersicum
<220> FEATURE:
<221> NAME/KEY: source
<222> LOCATION: 1..31
<223> OTHER INFORMATION: /mol_type="DNA"
      /organism="Solanum lycopersicum"

<400> SEQUENCE: 6
aggatatgca gcggacgggt tccaagggct t                              31

<210> SEQ ID NO 7
<211> LENGTH: 31
<212> TYPE: DNA
<213> ORGANISM: Solanum lycopersicum
<220> FEATURE:
<221> NAME/KEY: source
<222> LOCATION: 1..31
<223> OTHER INFORMATION: /mol_type="DNA"
      /organism="Solanum lycopersicum"

<400> SEQUENCE: 7
ctgaatggag aaggaaggcc tgccagtgtt g                              31

<210> SEQ ID NO 8
<211> LENGTH: 31
<212> TYPE: DNA
<213> ORGANISM: Solanum lycopersicum
<220> FEATURE:
<221> NAME/KEY: source
<222> LOCATION: 1..31
<223> OTHER INFORMATION: /mol_type="DNA"
      /organism="Solanum lycopersicum"

<400> SEQUENCE: 8
tctttcttgg ctgtttaact cgcgatgaac g                              31

<210> SEQ ID NO 9
<211> LENGTH: 31
<212> TYPE: DNA
<213> ORGANISM: Solanum lycopersicum
<220> FEATURE:
<221> NAME/KEY: source
<222> LOCATION: 1..31
```

```
<223> OTHER INFORMATION: /mol_type="DNA"
      /organism="Solanum lycopersicum"

<400> SEQUENCE: 9
aagaaaggtt ttggtctttc gcaaaaggca g                                    31
```

PEPINO MOSAIC VIRUS RESISTANT TOMATO PLANT

RELATED APPLICATIONS AND INCORPORATION BY REFERENCE

This application is a continuation-in-part application of international patent application Serial No. PCT/EP2012/071733 filed 2 Nov. 2012, which claims benefit of European patent application Serial No. 11187454.1 filed 2 Nov. 2011.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a tomato plant (*Solanum lycopersicum* L.) which may comprise a genetic determinant that confers resistance to Pepino Mosaic Virus (PepMV). The invention further relates to markers and the use of markers for identifying the presence of the genetic determinant that leads to PepMV resistance. The invention also relates to the seeds and progeny of such a plant and to propagation material for obtaining such a plant. Furthermore the invention relates to the use of plants, seeds and propagation material that comprise the genetic determinant as germplasm in a breeding programme.

BACKGROUND OF THE INVENTION

Commercial vegetable production, including the production of tomato, is affected by many conditions. The choice of the grower for a certain variety is a determining factor, and forms the genetic basis for the result that can be achieved. In addition, there are many external factors that influence the outcome. Growing conditions like climate, soil, and the use of inputs like fertilizer play a major role. In addition to this, the presence of pests and diseases also affects the total yield that can be reached.

Many diseases in tomato have been acknowledged a great while ago, in the early years of tomato cultivation. Breeders have in the meantime identified resistances to a great number of these diseases from various sources and have incorporated them in their products. Examples of these are resistance to Tobacco Mosaic Virus (TMV), which can infect a wide range of vegetables and other crops; *Fusarium oxysporum* f. sp. *lycopersicum*, and *Cladosporium fulvum* or "tomato leaf mold". Nowadays resistance against those diseases is more or less standard in all commercial tomato varieties. Whenever a new strain or related disease shows up, the search for new sources of resistance starts all over again. Knowledge of the disease and of the existing resistance to a possibly related form helps to determine new resistance sources relatively quickly. For some diseases however, and especially for pests, it is very difficult or has until now been impossible to develop material with a high level of resistance. Especially when resistance mechanisms are very complex, and rely on several genes that interact with each other, the challenge to develop a good level of resistance can be really high.

In addition, sometimes completely new diseases appear that are not related to any of the already known ones. For these, there is no indication yet what could be the most likely germplasm from which resistance can be developed. Neither is the resistance mechanism known, which also makes the development of a new resistance more complicated. As an additional complicating factor, a good bio-assay is needed to compare resistant plants with susceptible material. When little is known of a new pathogen, first the way in which it can infect a tomato plant has to be determined. A bio-assay that does not correlate with the conditions in the field of a grower could result in contradictory or unsatisfactory results. Too mild or too strong inoculation during a test will not generate useful material to work with for development of a resistant tomato plant in practice. In the end, the ultimate test is whether a resistance holds under a grower's conditions.

In 1999, a new virus occurred in commercial tomato production in Europe, especially in greenhouses. This virus could spread extremely quickly through a whole field, and neighbouring growers were easily affected. The virus was soon identified as Pepino Mosaic Virus, belonging to the Potex Group, which is characterised as highly infectious and persistent.

Pepino Mosaic Virus (PepMV) was first identified in 1974 on pepino or pear melon (*Solanum muricatum*), a South-American crop, on plants originating from Peru. It was at that time determined that tomatoes, and related wild species, could be infected, but without showing symptoms.

It is not yet determined how the virus could suddenly appear in European tomato productions, and later on also in e.g. Canada and the United States. Several different PepMV genotypes are identified and distinguished, among which are: LP, the original one from Peru; EU, from European greenhouses; CH1 and CH2 from Chile; and US1 and US2.

The PepMV isolates that are present in the commercial tomato crops are more virulent in tomato than isolates that are taken from a pepino crop, suggesting that the virus has genetically adapted. PepMV spreads very easily mechanically, through the usual activities that are done while working in a tomato crop. Very often therefore infected plants can be seen subsequently in a row. Also tools, clothes, etc. stay capable of transmitting the virus for several weeks, and PepMV can stay in dry plant material for as long as 3 months. It is very difficult to get rid of the virus once it has infected a tomato production.

Symptoms of PepMV are various and largely depend on the plant stage during infection, plant variety, plant vitality, and growing conditions. Sometimes symptoms are hardly visible, but the main symptom expressions include plants with 'nettle heads'—grayish, spiky plant tops—, stunted heads, chlorotic leafs or leaf spots, and uneven ripening, marbling, and blotching of the fruits. Symptoms are most apparent during fall and winter, under low light conditions and lower temperatures.

Losses of tomato production due to PepMV can also vary significantly, depending on the circumstances. In heavily infected crops, losses can probably reach up to 20%. The presence of other pathogens, for example *Verticilium* spp., can strongly influence the yield reduction as well.

Due to the very easy spread of PepMV, strict hygiene protocols have been implemented in many countries and by many growers. Since it is assumed that PepMV can also be transmitted through infected seeds, hygiene protocols for seed production and seed cleaning are also very strict.

Within the EU, tomato seed has to be free from PepMV when it is imported or traded. EU members are required to do surveys to determine the absence of the virus on tomato seeds.

Since it was found to be very difficult to eradicate the virus after it had infected a commercial growing, nowadays many growers rely on 'cross-protection': inoculation of the crop with a mild PepMV isolate, to prevent the severe symptoms that are caused by aggressive isolates. This system however brings several risks. The combination of certain mild with certain aggressive isolates, especially when they originate from different genotypes, can enhance instead of diminish symptoms (Hanssen et al, Plant Pathology 59, 13-21 (2010)). Since it is not known in advance which aggressive isolate will occur in a certain area or certain season, the possibly harmful combination cannot be prevented. In addition, it is not even always clear which mild isolate is being used because the identification is rather difficult.

Another risk of combining viral genotypes is the possibility of genetic recombination between the strains, which can result in new and potentially even more devastating virus isolates (Hanssen et al., European Journal of Plant Pathology 121, 131-146 (2008); Hasiow-Jaroszewska et al., Acta Biochimica Polonica 57, 385-388 (2010)).

Although the search for sources of resistance to PepMV in tomato has been intensive from the start, until now no resistant *Solanum lycopersicum* plants are available. The genetic makeup of the resistance, and the bio-assay for screening, are so complex, that no reports or notices of cultivated tomato material with PepMV resistance are known. Durable resistance has only been found in *Solanum ochranthum*, which cannot be crossed with cultivated tomato.

Citation or identification of any document in this application is not an admission that such document is available as prior art to the present invention.

SUMMARY OF THE INVENTION

It is an object of the present invention to provide tomato plants (*Solanum lycopersicum* L.) that carry a genetic determinant which leads to resistance to Pepino Mosaic Virus.

It is an object of the present invention to provide QTLs that contribute to Pepino Mosaic Virus resistance in tomato plants (*Solanum lycopersicum*).

It is a further object of the present invention to provide markers that can identify the genetic determinant leading to PepMV resistance.

The present invention thus provides a tomato plant (*Solanum lycopersicum*) which may comprise a genetic determinant that confers resistance to Pepino Mosaic Virus (PepMV), wherein the resistance is characterised by the presence of at least:

QTL1 or a PepMV-resistance-conferring part thereof, located on Linkage Group (LG) 6 between the physical positions 32,363,349 bp and 34,505,939 bp, preferably between positions 33,558,627 bp and 34,505,939 bp, and/or QTL2 or a PepMV-resistance-conferring part thereof, located on LG 7 between the physical positions 60,667, 821 bp and 62,460,220 bp, preferably between positions 61,387,356 bp and 62,253,846 bp, and/or QTL3 or a PepMV-resistance-conferring part thereof, located on LG 9 between the physical positions 60,998, 420 bp and 62,512,587 bp, preferably between positions 61,494,664 bp and 62,385,023 bp, more preferably between positions 61,723,339 bp and 62,385,023 bp.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

Deposits

Seeds of *Solanum lycopersicum* 11R.412000 and 11R.446400 that comprise genetic determinants of the invention which lead to resistance to Pepino Mosaic Virus, were deposited with NCIMB Ltd, Ferguson Building, Craibstone Estate, Bucksburn, Aberdeen AB21 9YA, UK on 13 Jan. 2012 under deposit accession number NCIMB 41927 and NCIMB 41928, respectively.

Seeds of *Solanum lycopersicum* 12R.4211014 which may comprise QTL1 and QTL2, and seeds of *Solanum lycopersicum* T 12R.107, which may comprise the genetic determinant of the invention which may comprise QTL1 and QTL2 and QTL3, which QTLs lead to resistance to Pepino Mosaic Virus, was deposited with NCIMB Ltd, Ferguson Building, Craibstone Estate, Bucksburn, Aberdeen AB21 9YA, UK on Oct. 10, 2012 under deposit accession numbers NCIMB 42068 and NCIMB 42069 respectively.

The deposited seeds do not meet the DUS criteria which are required for obtaining plant variety protection, and may therefore not be considered to be plant varieties.

The Deposits with NCIMB Ltd, under deposit accession numbers 41927, 41928, 42068 and 42069 were made pursuant to the terms of the Budapest Treaty. Upon issuance of a patent, all restrictions upon the deposit will be removed, and the deposit is intended to meet the requirements of 37 CFR §§1.801-1.809. The deposit will be irrevocably and without restriction or condition released to the public upon the issuance of a patent. The deposit will be maintained in the depository for a period of 30 years, or 5 years after the

DETAILED DESCRIPTION OF THE INVENTION

The identification of a complex resistance mechanism that consists of more than one QTL is a tough and intricate process. No indication of the genetic background for this resistance was known. Furthermore, no reliable PepMV screening method for *S. lycopersicum* was publicly available either. An additional complicating factor in the development of the present invention was therefore the challenge to design a good and reliable bio-assay for *S. lycopersicum* that would generate results that relate well to a grower's conditions.

Research that led to the present invention furthermore showed that the genetic determinant of the invention that leads to PepMV resistance may comprise more than one QTL and that those QTLs are located on separate chromosomes of the *Solanum lycopersicum* genome. This is an additional complicating factor for the creation of resistant plants.

In one embodiment the PepMV resistance is characterised by the presence of at least:
QTL1 or a PepMV-resistance-conferring part thereof and
 QTL2 or a PepMV-resistance-conferring part thereof,
or
QTL1 or a PepMV-resistance-conferring part thereof and
 QTL3 or a PepMV-resistance-conferring part thereof,
or
QTL2 or a PepMV-resistance-conferring-part thereof and
 QTL3 or a PepMV-resistance-conferring part thereof.

In one embodiment, the resistance is characterised by the presence of QTL1 or a PepMV-resistance-conferring part thereof, and QTL2 or a PepMV-resistance-conferring part thereof, and QTL3 or a PepMV-resistance-conferring part thereof.

The combination of two or more resistance-conferring QTLs leads to a higher level of resistance to Pepino Mosaic Virus.

In one embodiment, the invention relates to a *Solanum lycopersicum* plant carrying a genetic determinant that may comprise one or more of QTL1, QTL2 and QTL3, which genetic determinant confers resistance to Pepino Mosaic Virus, and which QTLs are as comprised in tomato plants representative seed of which were deposited with the NCIMB under deposit numbers NCIMB 41927, NCIMB 41928, NCIMB 42068, and NCIMB 42069.

In one embodiment, said determinant is introgressed from a plant grown from seed that was deposited with the NCIMB under accession number NCIMB 41927, and/or from a plant grown from seed that was deposited with the NCIMB under accession number NCIMB 41928, and/or from a plant grown from seed that was deposited with the NCIMB under accession number NCIMB 42068, and/or from a plant grown from seed that was deposited with the NCIMB under accession number NCIMB 42069.

In a certain aspect of the invention, the one or more of the QTLs 1, 2 and 3 that are introgressed into a *Solanum lycopersicum* plant consist of a resistance conferring part thereof.

"Introgression" as used herein is intended to mean introduction of a genetic determinant into a plant not carrying the genetic determinant by means of crossing and selection in the first generation in which the trait becomes visible. For a dominant trait, selection may start in the F1 of a cross between a plant with the trait and a plant without the trait. For a recessive trait this is suitably the F2. Alternatively and for a polygenic trait preferably, selection is done with the assistance of molecular markers that are linked to the QTLs. Marker assisted selection may be done in any generation or population that may comprise plants carrying any number of desired QTLs.

Deposit number NCIMB 41927 or progeny seed thereof, or deposit number NCIMB 42068 or progeny seed thereof, may suitably be used as a source to introgress QTL1, located on LG 6, and/or QTL2, located on LG 7 into a *Solanum lycopersicum* plant. In NCIMB 41927 and NCIMB 42068 QTL1 is linked to SEQ ID NO:1, and SEQ ID NO:4, and SEQ ID NO:5; QTL2 is linked to SEQ ID NO:2, and SEQ ID NO:6, and SEQ ID NO:7. Deposit number NCIMB 41928 or progeny seed thereof may be used as the source to introgress QTL2, located on LG7, and/or QTL3, located on LG9. In NCIMB 41928 QTL2 is linked to SEQ ID NO:2, and SEQ ID NO:6, and SEQ ID NO:7; QTL3 is linked to SEQ ID NO:3, and SEQ ID NO:8, and SEQ ID NO:9.

Deposit number NCIMB 42069 or progeny seed thereof may be used as the source to introgress QTL1, located on LG6, and/or QTL2, located on LG7, and/or QTL3, located on LG9. In NCIMB 42069 QTL1 is linked to SEQ ID NO:1, and SEQ ID NO:4, and SEQ ID NO:5; QTL2 is linked to SEQ ID NO:2, and SEQ ID NO:6, and SEQ ID NO:7; QTL3 is linked to SEQ ID NO:3, and SEQ ID NO: 8, and SEQ ID NO:9.

The SEQ ID Numbers are defined in Table 2.

In one embodiment, one or more of the QTLs of the invention that confer resistance to Pepino Mosaic Virus in tomato are present in homozygous form. With respect to the trait of the invention, plants that carry the resistance trait may suitably be identified among descendants from a cross between a plant not carrying the trait, and a plant that does carry the said trait, by growing F2 plants from seeds that are the result from the initial cross and a selfing step, and selecting plants showing the desired trait. Selecting the plants may be done phenotypically through a bio-assay, or may be done through identification of one or more of the QTLs of the invention, or a resistance-conferring part thereof, that contribute to the trait, by marker assisted selection.

One or two or all three of the QTLs of the invention confer the resistance in a recessive way. The corresponding phenotypic trait, resistance to PepMV, is then consequently also inherited in a recessive way. When all three QTLs confer the resistance in a recessive way, a large population of F2 plants has to be grown to select plants that have the phenotypic trait, and/or that carry all three of the QTLs of the invention. Alternatively, selection may start for a lower level of resistance and/or for one or two of the QTLs of the invention. The separate genetic determinants conferring the resistance may also be inherited in an intermediate manner, or in a dominant manner. Selection for the phenotypic trait is easier when intermediate or dominant inheritance is involved. A combination of recessive and/or intermediate and/or dominant QTLs to obtain the highest level of resistance may occur.

Selection may be done on phenotype, or on the presence of said resistance-conferring QTLs of the invention. Selection may also be done by using one or more molecular markers. The use of molecular markers requires a smaller population for screening, and may be done in a very early stage.

In one embodiment, a tomato plant of the invention may comprise:
- QTL1 or a resistance conferring part thereof, which in deposits NCIMB 41927 and/or NCIMB 42068 and/or NCIMB 42069 is linked to molecular markers characterized by SEQ. ID No. 1, SEQ ID NO:4, and SEQ ID NO:5 (Table 2), and/or
- QTL2 or a resistance conferring part thereof, which in deposits NCIMB 41927 and/or NCIMB 41928 and/or NCIMB 42068 and/or NCIMB 42069 is linked to molecular markers characterized by SEQ. ID No. 2, SEQ ID NO:6, and SEQ ID NO:7 (Table 2), and/or
- QTL3 or a resistance conferring part thereof, which in deposits NCIMB 41928 and/or NCIMB 42069 is linked to molecular markers characterized by SEQ. ID No. 3, SEQ ID NO:8, and SEQ ID NO:9 (Table 2).

In one embodiment, a tomato plant of the invention may comprise QTL1, which is preferably associated with a molecular marker characterized by SEQ. ID No. 1, and/or SEQ ID NO:4, and/or SEQ ID NO:5; and QTL2, which is preferably associated with a molecular marker characterized by SEQ. ID No. 2, and/or SEQ ID NO:6, and/or SEQ ID NO:7; and QTL3, which is preferably associated with a molecular marker characterized by SEQ. ID No. 3, and/or SEQ ID NO:8, and/or SEQ ID NO:9. Representative seeds of such a plant of the invention are deposited as NCIMB 42069.

It was found according to the invention that QTL1 is located on chromosome 6 of the tomato genome between the physical positions 32,363,349 bp and 34,505,939 bp and could be identified by the presence of a molecular SNP marker. This SNP marker is located at 34,456,931 bp on the public physical map of the *Solanum lycopersicum* genome version SL 2.40, and is characterized by SEQ ID NO:1 (Table 2). Further molecular SNP markers, which may be used to demarcate the QTL1 region, are characterized by SEQ ID NO:4 at 33,558,627 bp and SEQ ID NO:5 at 34,505,939 bp (Table 2). In plants of deposits NCIMB 41927 and NCIMB 42068 and NCIMB 42069 these SNP markers indicate and are linked to QTL1, and are therefore also indicative of resistance to PepMV in plants of those deposits.

A second QTL contributing to PepMV resistance, QTL2, is positioned on chromosome 7 between the physical positions 60,667,821 bp and 62,460,220 bp. QTL2 could be identified by the presence of a SNP marker which is located at a physical position of 61,550,890 bp on the public map of the *Solanum lycopersicum* genome version SL 2.40, and is characterized by SEQ ID NO:2 (Table 2). Further molecular SNP markers, which may be used to demarcate the QTL2 region, are characterized by SEQ ID NO:6 at 61,387,356 bp and SEQ ID NO:7 at 62,253,846 bp (Table 2). In plants of deposits NCIMB 41927 and NCIMB 41928 and NCIMB 42068 and NCIMB 42069 these SNP markers indicate and are linked to QTL2, and are therefore also indicative of resistance to PepMV in plants of those deposits.

The third QTL that leads to PepMV resistance, QTL3, is located on chromosome 9 between the physical positions 60,998,420 bp and 62,512,587 bp. The presence of this QTL could be detected by a SNP marker located at 61,603,006 bp on the public physical map of the *Solanum lycopersicum* genome version SL 2.40 which SNP marker is characterized by SEQ ID NO:3 (Table 2). Further molecular SNP markers, which may be used to identify the QTL3 region, are characterized by SEQ ID NO:8 at 61,872,648 bp and SEQ ID NO:9 at 62,191,735 bp (Table 2). In plants of deposits NCIMB 41928 and NCIMB 42069 these SNP markers indicate and are linked to QTL3 and are therefore also indicative of resistance to PepMV in plants of those deposits.

In one embodiment, a tomato plant which may comprise a genetic determinant that confers resistance to Pepino Mosaic Virus (PepMV), is obtainable by identifying the presence of QTL1 or a PepMV-resistance-conferring part thereof, and/or QTL2 or a PepMV-resistance-conferring part thereof, and/or QTL3 or a PepMV-resistance-conferring part thereof, whereby the QTLs 1 to 3 are defined as:
- QTL1, located on Linkage Group (LG) 6 between the physical positions 32,363,349 bp and 34,505,939 bp, preferably between positions 33,558,627 bp and 34,505,939 bp;
- QTL2, located on LG 7 between the physical positions 60,667,821 bp and 62,460,220 bp, preferably between positions 61,387,356 bp and 62,253,846 bp;
- QTL3, located on LG 9 between the physical positions 60,998,420 bp and 62,512,587 bp, preferably between positions 61,494,664 bp and 62,385,023 bp, more preferably between positions 61,723,339 bp and 62,385,023 bp.

In one embodiment, the invention relates to a tomato plant obtainable by a method which may comprise:
a) crossing a plant which may comprise QTL1 and QTL2, representative seed of which was deposited as NCIMB 41927 or NCIMB 42068, or a plant which may comprise QTL2 and QTL3, representative seed of which was deposited as NCIMB 41928, with a plant not comprising the genetic determinants to obtain an F1 population;
b) optionally performing one or more rounds of selfing and/or crossing a plant from the F1 to obtain a further generation population;
c) c) selecting a plant that may comprise QTL1 and/or QTL2 from the population, or a plant that may comprise QTL2 and/or QTL3;
d) crossing a selected plant that may comprise QTL1 and/or QTL2 with a plant which may comprise QTL2 and QTL3, representative seed of which was deposited as NCIMB 41928, or crossing a selected plant that may comprise QTL2 and/or QTL3 with a plant which may comprise QTL1 and QTL2 representative seed of which was deposited as NCIMB 41927 or NCIMB 42068;
e) selfing a plant obtained in step d) to obtain a segregating population;
f) selecting a plant that may comprise QTL1 and QTL2, or QTL2 and QTL3, or QTL1 and QTL3, or QTL1 and QTL2 and QTL3.

Either QTL1 and/or QTL2 may be introgressed first, or QTL2 and/or QTL3 are introgressed first into a *Solanum lycopersicum* plant lacking either of the QTLs, followed by the introduction of QTL2 and/or QTL3, or QTL1 and/or QTL2. Subsequent selection is done for one or two or three of the said QTLs involved in Pepino Mosaic Virus resistance.

In a further embodiment, the invention relates to a tomato plant that carries the genetic determinant that leads to resistance against Pepino Mosaic Virus, obtainable by a method which may comprise:
a) crossing a plant which may comprise QTL1 and QTL2, representative seed of which was deposited as NCIMB 41927 or NCIMB 42068, or a plant which may comprise QTL2 and QTL3, representative seed of which was deposited as NCIMB 41928, or a plant which may comprise QTL1 and QTL2 and QTL3 representative seed of which was deposited as NCIMB 42069 with a plant not which may comprise the genetic determinant to obtain an F1 population;
b) performing one or more rounds of selfing and/or crossing a plant from the F1 to obtain a further generation population;
c) optionally selecting a plant from the population that may comprise one or two of the QTLs 1, 2 and 3, followed by crossing with a plant which may comprise at least the other QTLs of QTL 1, 2 and 3, and subsequently repeating step b);
d) selecting a plant that may comprise QTL1 and QTL2 and QTL3.

In a further embodiment, a tomato plant of the invention is obtainable by crossing a first parent plant that may comprise QTL1 and/or QTL2 and/or QTL3 with a second parent plant that may comprise QTL1 and/or QTL2 and/or QTL3 and selecting in subsequent generations, optionally after further selfing and/or crossing steps, for a plant that may comprise QTL1 and QTL2, or QTL 1 and QTL3, or QTL2 and QTL3, or QTL1 and QTL2 and QTL3.

In a further embodiment, a plant grown from seed deposited as NCIMB 41927 or a plant grown from seed deposited as NCIMB 42068 is crossed with a plant grown from seed deposited as NCIMB 41928, the resulting F1 is selfed, and subsequent selection for plants which may comprise QTL1 and/or QTL2 and/or QTL3 is performed. In a preferred aspect, selection is done for a plant which may comprise all three QTLs, preferably homozygously, which plant is highly resistant or immune to Pepino Mosaic Virus.

In a preferred embodiment, the invention relates to a tomato plant obtainable by a method which may comprise:
a) crossing a plant which may comprise QTL1 and QTL2 and QTL3, representative seed of which was deposited as NCIMB 42069, with a plant not comprising the said QTLs to obtain an F1 population;
b) performing one or more rounds of selfing and/or crossing a plant from the F1 to obtain a further generation population;
c) optionally selecting a plant from the population that may comprise one or two of the QTLs 1, 2 and 3, followed by crossing with a plant which may comprise at least the other QTLs of QTL 1, 2 and 3, and subsequently repeating step b);
d) selecting a plant that may comprise QTL1 and QTL2 and QTL3.

The process for obtaining a *Solanum lycopersicum* plant of the invention which may comprise any number of QTLs 1, 2, and/or 3, preferably QTL1 and QTL2 and QTL3, more preferably all QTL1 and QTL2 and QTL3 homozygously, may be performed in various manners which are known to the skilled person. The sources to be used for obtaining the said plant are suitably a plant which may comprise QTL1 or QTL2 or QTL3, a plant which may comprise QTL1 and QTL2 or QTL2 and QTL3 or QTL1 and QTL3, or a plant which may comprise QTL1 and QTL2 and QTL3. Representative seeds of suitable sources which may comprise QTL1 and QTL2 were deposited with the NCIMB under deposit numbers NCIMB 41927 or NCIMB 42068, and representative seeds of a suitable source which may comprise QTL2 and QTL3 were deposited as NCIMB 41928.

Representative seeds of a suitable source which may comprise QTL1 and QTL2 and QTL3 were deposited with the NCIMB under deposit number NCIMB 42069.

It is clear that the parent that provides one or more genetic determinants of the invention is not necessarily a plant grown directly from the deposited seeds. The parent may also be a progeny plant from the seed, or a progeny plant from seeds that are identified to have the genetic determinant which may comprise one or two or three of the QTLs of the invention by other means.

Resistance to Pepino Mosaic Virus is a reduction or absence of symptoms that are a result of Pepino Mosaic Virus infection, either through natural infection or artificial infection such as inoculation. The reduction or absence of symptoms is as compared to a *Solanum lycopersicum* plant not carrying the genetic determinant or one or more QTLs of the invention, as tested according to for example Example 2.

In a preferred aspect of the invention, the homozygous presence of QTL1 and the homozygous presence of QTL2 and the homozygous presence of QTL3 results in the highest level of resistance or immunity. The highest level of resistance or immunity is inherited in a recessive way.

The resistance of the invention is preferably immunity. Immunity is defined as a resistance system wherein the virus particles do not, or not significantly, accumulate in the plant after inoculation or infection. Immunity may be measured through an ELISA assay on virus particles, which assay is well known to a skilled person. Immunity gives a low or negative score in an ELISA assay. A low or a negative score indicates a virus titer that is comparable to a non-virus-infected plant. Immunity is suitably conferred by the presence of at least QTL1 and QTL2 and QTL3 in homozygous form.

The invention furthermore relates to a cell of a tomato plant as claimed. Such cell may be either in isolated form or may be part of the complete tomato plant or parts thereof and then still constitutes a cell of the invention because such a cell harbours in its genetic constitution the genetic information that leads to the resistance characteristics that define the tomato plant of the invention. Each cell of tomato plants of the invention carries the genetic information that leads to phenotypic expression of said trait. Such a cell of the invention may also be a regenerable cell that may be used to regenerate a new tomato plant of the invention.

The invention also relates to tissue of a plant as claimed. The tissue may comprise cells that harbour in their genetic constitution the genetic information that leads to the resistance characteristics that define the tomato plant of the invention. The tissue may be undifferentiated tissue or already differentiated tissue. Undifferentiated tissues are for example stem tips, anthers, petals, pollen and may be used in micropropagation to obtain new plantlets that are grown into new plants of the invention. The tissue may also be grown from a cell of the invention.

The invention according to a further aspect thereof relates to seeds of a plant as claimed. Although the seeds do not show the genetic trait of the tomato plant of the invention, they harbour the genetic information that leads to the resistance characteristics that when a plant is grown from the seeds makes this plant a plant of the invention.

The invention also relates to progeny of the plants, cells, tissues and seeds of the invention. Such progeny may in itself be plants, cells, tissues or seeds.

As used herein the word "progeny" is intended to mean the first and all further descendants from a cross with a plant of the invention that may comprise a genetic determinant that leads to PepMV resistance. Progeny of the invention are descendants of any cross with a plant of the invention that carries the trait that leads to PepMV resistance. In one embodiment, progeny plants of the invention carry one or more of the QTL1, QTL2 and QTL3 that constitute the genetic determinant of the invention that leads to resistance to Pepino Mosaic Virus (PepMV). Preferably, progeny may comprise two or more of the QTL1, QTL2 and QTL3, more preferably all three QTL1, QTL2 and QTL3 as defined herein.

Progeny plants preferably show at least some level of resistance to Pepino Mosaic Virus, in particular a high level of resistance and more in particular immunity against Pepino Mosaic Virus.

"Progeny" also encompasses plants that carry the genetic determinant that causes the PepMV resistance trait of the invention and are obtained from other plants or progeny of plants of the invention by vegetative propagation or multiplication.

The invention thus further relates to seed of the claimed plant and to parts of the plant that are suitable for sexual reproduction. Such parts are for example selected from the group consisting of microspores, pollen, ovaries, ovules, embryo sacs and egg cells. In addition, the invention relates to parts of the plant that are suitable for vegetative reproduction, in particular cuttings, roots, stems, cells, and protoplasts.

According to a further aspect thereof the invention provides a tissue culture of the claimed plant. The tissue culture may comprise regenerable cells. Such tissue culture may be derived from leaves, pollen, embryos, cotyledons, hypocotyls, meristematic cells, roots, root tips, anthers, flowers, seeds and stems. The tissue culture may be regenerated into a plant carrying the genetic determinant of the invention. Suitably a regenerated plant expresses the phenotype of Pepino Mosaic Virus resistance.

The invention furthermore relates to hybrid seed and to a method of producing hybrid seed which may comprise crossing a first parent plant with a second parent plant and harvesting the resultant hybrid seed, wherein said first parent plant and/or said second parent plant is the plant as claimed.

The invention also relates to inbreds and doubled haploids that carry the PepMV resistance trait of the invention.

In one embodiment, the invention relates to tomato plants of the invention that carry the genetic determinant of the invention which leads to PepMV resistance, and that have acquired said determinant by introduction of the genetic information that is responsible for the trait from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

In one embodiment, the source from which a genetic determinant of the invention is acquired is formed by plants grown from seeds of which a representative sample was deposited under accession number NCIMB 41927, or under accession number NCIMB 41928, or under accession number 42068, or under accession number NCIMB 42069, or from the deposited seeds, or from sexual or vegetative descendants thereof, or from another source which may comprise the genetic determinant, or from a combination of these sources.

In a preferred embodiment, the invention relates to non-transgenic *Solanum lycopersicum* plants. The source for acquiring one or more of QTL1, QTL2 or QTL3 of the invention, to obtain a plant of the invention that is resistant to Pepino Mosaic Virus, is suitably a *Solanum lycopersicum* plant that carries the QTLs 1 and/or 2 and/or 3 as comprised in NCIMB 41927 and/or NCIMB 41928 and/or NCIMB 42068 and/or NCIMB 42069, or alternatively a plant of a *Solanum* species that carries one or more of the said QTLs and that may be crossed with *Solanum lycopersicum*. Optionally after crossing with a related species, techniques such as embryo rescue, backcrossing, or other techniques known to the skilled person may be performed to obtain seeds of the interspecific cross, which seeds may be used as the source for further development of a non-transgenic *Solanum lycopersicum* plant that shows resistance to Pepino Mosaic Virus.

The invention also relates to the germplasm of plants of the invention. The germplasm is constituted by all inherited characteristics of an organism and according to the invention encompasses at least the trait of the invention. The germplasm may be used in a breeding programme for the development of PepMV resistant tomato plants.

The invention also relates to a tomato fruit that is produced by a plant of the invention. The invention further relates to a food product, which may comprise the fruit of a tomato plant as claimed, or parts thereof. The invention also relates to a food product in processed form.

In one aspect the invention relates to a method for production of a tomato plant which may comprise resistance to Pepino Mosaic Virus, which may comprise:

a) crossing a plant which may comprise QTL1 and QTL2, representative seed of which was deposited as NCIMB 41927 and NCIMB 42068, or a plant which may comprise QTL2 and QTL3, representative seed of which was deposited as NCIMB 41928, with a plant not comprising the genetic determinants to obtain an F1 population;

b) optionally performing one or more rounds of selfing and or crossing a plant from the F1 to obtain a further generation population;

c) selecting a plant that may comprise QTL1 and/or QTL2 from the population, or a plant that may comprise QTL2 and/or QTL3;

d) crossing a selected plant that may comprise QTL1 and/or QTL2 with a plant which may comprise QTL2 and QTL3, representative seed of which was deposited as NCIMB 41928, or crossing a selected plant that may comprise QTL2 and/or QTL3 with a plant which may comprise QTL1 and QTL2 representative seed of which was deposited as NCIMB 41927 and NCIMB 42068;

e) selfing a plant obtained in step d) to obtain a segregating population;

f) selecting a plant that may comprise QTL1 and QTL2, or QTL2 and QTL3, or QTL1 and QTL3, or QTL1 and QTL2 and QTL3.

The invention further relates to a method for the production of a tomato plant which may comprise resistance to Pepino Mosaic Virus, which may comprise:

a) crossing a plant which may comprise QTL1 and QTL2, representative seed of which was deposited as NCIMB 41927 or NCIMB 42068, or a plant which may comprise QTL2 and QTL3, representative seed of which was deposited as NCIMB 41928, or a plant which may comprise QTL1 and QTL2 and QTL3 representative seed of which was deposited as NCIMB 42069 with a plant not comprising the genetic determinant to obtain an F1 population;

b) performing one or more rounds of selfing and/or crossing a plant from the F1 to obtain a further generation population;

c) optionally selecting a plant from the population that may comprise one or two of the QTLs 1, 2 and 3, followed by crossing with a plant which may comprise at least the other QTLs of QTL 1, 2 and 3, and subsequently repeating step b);

d) selecting a plant that may comprise QTL1 and QTL2 and QTL3.

In one aspect the invention relates to a method for production of a tomato plant which may comprise resistance to Pepino Mosaic Virus by crossing a first parent plant that may comprise QTL1 and/or QTL2 and/or QTL3 with a second parent plant that may comprise QTL1 and/or QTL2 and/or QTL3 and selecting in subsequent generations, optionally after further selfing and/or crossing steps, for a plant that may comprise QTL1 and QTL2, or QTL 1 and QTL3, or QTL2 and QTL3, or QTL1 and QTL2 and QTL3.

In a preferred aspect, the invention relates to a method for the production of a tomato plant which may comprise:

a) crossing a plant which may comprise QTL1 and QTL2 and QTL3, representative seed of which was deposited as NCIMB 42069, with a plant not comprising the said QTLs to obtain an F1 population;

b) performing one or more rounds of selfing and/or crossing a plant from the F1 to obtain a further generation population;

c) optionally selecting a plant from the population that may comprise one or two of the QTLs 1, 2 and 3, followed by crossing with a plant which may comprise at least the other QTLs of QTL 1, 2 and 3, and subsequently repeating step b);

d) selecting a plant that may comprise QTL1 and QTL2 and QTL3.

The invention additionally provides a method of introducing a desired trait into a tomato plant which may comprise resistance to Pepino Mosaic Virus, which may comprise:

a) crossing a tomato plant which may comprise resistance to Pepino Mosaic Virus, representative seed of which were deposited with the NCIMB under deposit number NCIMB 41927 and NCIMB 41928 and NCIMB 42068 and NCIMB 42069, with a second tomato plant that may comprise a desired trait to produce F1 progeny;

b) selecting an F1 progeny that may comprise resistance to Pepino Mosaic Virus and the desired trait;

c) crossing the selected F1 progeny with either parent, to produce backcross progeny;

d) selecting backcross progeny which may comprise the desired trait and resistance to Pepino Mosaic Virus; and e) optionally repeating steps c) and d) one or more times in succession to produce selected fourth or higher backcross progeny that may comprise the desired trait and resistance to Pepino Mosaic Virus. The invention includes a tomato plant produced by this method and the tomato fruit obtained therefrom.

Selection for a plant which may comprise a genetic determinant of the invention may alternatively be done following any crossing or selfing step of the method.

In one embodiment the plant which may comprise the genetic determinant is a plant of an inbred line, a hybrid, a doubled haploid, or of a segregating population.

The invention further provides a method for the production of a tomato plant which may comprise resistance to Pepino Mosaic Virus by using a doubled haploid generation technique to generate a doubled haploid line which may comprise the said genetic determinant that leads to resistance to Pepino Mosaic Virus.

The invention furthermore relates to hybrid seed and to a method for producing hybrid seed which may comprise crossing a first parent plant with a second parent plant and harvesting the resultant hybrid seed, wherein said first parent plant and/or said second parent plant is the plant as claimed.

In one embodiment, the invention relates to a method for producing a hybrid tomato plant which may comprise crossing a first parent tomato plant with a second parent tomato plant and harvesting the resultant hybrid tomato seed, in which the first parent tomato plant and/or the second parent tomato plant may comprise a genetic determinant of the invention that leads to resistance to Pepino Mosaic Virus, in particular the genetic determinant described herein.

The invention also relates to a method for the production of a tomato plant which may comprise resistance to Pepino Mosaic Virus by using a seed that may comprise a genetic determinant in its genome that leads to resistance to Pepino Mosaic Virus for growing the said tomato plant. The seeds are suitably seeds of which a representative sample was deposited with the NCIMB under deposit numbers NCIMB 41927 or NCIMB 41928 or NCIMB 42068 or NCIMB 42069.

The invention also relates to a method for seed production which may comprise growing tomato plants which may comprise resistance to Pepino Mosaic Virus, allowing the plants to produce seeds, and harvesting those seeds. Production of the seeds is suitably done by crossing or selfing.

In one embodiment, the invention relates to a method for the production of a tomato plant which may comprise resistance to Pepino Mosaic Virus by using tissue culture. The invention furthermore relates to a method for the production of a tomato plant which may comprise resistance to Pepino Mosaic Virus by using vegetative reproduction.

In one embodiment, the invention relates to a method for the production of a tomato plant which may comprise resistance to Pepino Mosaic Virus by using a method for genetic modification to introduce the genetic determinant of the invention that leads to resistance to Pepino Mosaic Virus into the tomato plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of tomato plants that comprise resistance to Pepino Mosaic Virus wherein germplasm which may comprise a genetic determinant that leads to resistance to Pepino Mosaic Virus is used. Representative seed of said plant which may comprise a genetic determinant was deposited with the NCIMB under deposit numbers NCIMB 41927 and NCIMB 41928 and NCIMB 42068 and NCIMB 42069.

In a further embodiment the invention relates to a method for the production of a tomato plant which may comprise resistance to Pepino Mosaic Virus wherein progeny or propagation material of a plant which may comprise a genetic determinant of the invention conferring said resistance to Pepino Mosaic Virus is used as a source to introgress resistance to Pepino Mosaic Virus into another tomato plant. Representative seed of said plant which may comprise a genetic determinant was deposited with the NCIMB under deposit numbers NCIMB 41927 and NCIMB 41928 and NCIMB 42068 and NCIMB 42069.

The invention provides preferably a tomato plant showing resistance to Pepino Mosaic Virus, which plant is obtainable by any of the methods herein described.

The invention also relates to a method for the production of tomato fruits, which may comprise growing PepMV resistant tomato plants as described herein and allowing them to produce tomato fruits and optionally harvesting the fruits.

The term 'genetic determinant' and 'genetic determinants' as used herein encompasses one or more of the QTLs, genes, or alleles as described herein. These terms are used interchangeably.

In one aspect the invention relates to a molecular SNP marker present in a *Solanum lycopersicum* genome, which molecular SNP marker is genetically linked to a QTL that confers resistance to Pepino Mosaic Virus in *Solanum lycopersicum*, and which molecular SNP marker is characterised by any of the SEQ ID NOs:1-9. The SEQ ID NOs:1-9 are defined in Table 2.

In a further aspect the invention relates to the use of a molecular marker characterized by any of the SEQ ID NOs:1-9 as defined in Table 2 for identifying a Pepino Mosaic Virus resistance conferring QTL in a *Solanum lycopersicum* plant.

A genetic determinant or QTL may be identified by the use of a molecular marker. A genetic determinant or QTL may alternatively be identified by the position on a genetic map, or by indication of the location on a linkage group or chromosome. When a genetic determinant or QTL is not linked to a specific molecular marker any longer, but its position on a chromosome as defined on a genetic map is unaltered, this genetic determinant is still the same as when it was linked to the molecular marker. The genetic trait that it confers is therefore also still the same.

The 'genetic trait' is the trait or characteristic that is conferred by the genetic determinant. The genetic trait may be identified phenotypically, for example by performing a bio-assay. However, also plant stages for which no phenotypic assay may be performed do carry the genetic information that leads to the genetic trait. 'Trait' or 'phenotypic trait' may be used instead of 'genetic trait'. Furthermore, in case of a recessive trait heterozygous plants also carry genetic information that when present in homozygous form causes the PepMV resistance trait. Such plants are a source of the resistance alleles and as such are also part of this invention.

In the absence of molecular markers, or in the instance that recombination between the genetic determinant and the marker has taken place so that the marker is not predictive anymore, equivalence of genetic determinants may be determined by an allelism test. To perform an allelism test, a tester plant which is homozygous for the known determinant of the invention is crossed with material to be tested that is also homozygous for its genetic determinant. When no segregation for the trait to be observed is present in the F2 of the cross, the genetic determinants have been proven to be equivalent or the same.

When more than one gene is responsible for a certain trait, and an allelism test is done to determine equivalence, the skilled person doing the test has to make sure that all relevant genes are present homozygously for the test to work properly.

Genetic maps may vary according to the method by which they are assembled. A person skilled in the art knows how to compare and combine genetic maps, whereby differences between genetic maps may be eliminated or minimized. Information from one genetic map may therefore be transferred or translated to another genetic map. The positions as used herein are physical positions based on the public physical map of the tomato genome, release SL2.40 of January 2011 (http://solgenomics.net/genomes/Solanum_lycopersicum/genome_data.pl).

Resistance to Pepino Mosaic Virus based on the genetic determinant of the invention may comprise resistance to one or more known PepMV genotypes. Known genotypes include LP, EU, CH1, CH2, US1 and US2 which are known to the skilled person. Resistance to Pepino Mosaic Virus may in addition comprise resistance to a PepMV genotype that has currently not yet been identified. A not yet identified PepMV genotype may be a genotype that is presently infecting plants, but has not yet been characterised as belonging to Pepino Mosaic Virus. It may also be a new PepMV genotype that has developed from existing strains, or another genotype that will also be classified as being Pepino Mosaic Virus.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Creation of Tomato Plants of the Invention

In research that led to the present invention, a *S. peruvianum* plant that was immune for Pepino Mosaic Virus was identified in the applicant's germplasm by means of performing bio-assays (see Example 2) for Pepino Mosaic Virus resistance. The immunity level of the resistance was repeatedly confirmed by consecutive bio-assays. The identification of immunity in *S. peruvianum* was very surprising, since although many accessions have been screened in various studies, no earlier reports of immune or highly resistant plants in *S. peruvianum* have been given.

No other *S. peruvianum* plants containing immunity against PepMV were identified in the bio-assay. The single immune plant was self-incompatible, and therefore no selfed seeds could be obtained. As the inheritance for immunity to PepMV was expected to be complex, crossing with another *S. peruvianum* plant, followed by selfing and selection for the resistance, was thought to be a too risky approach for maintaining the immunity. Therefore the plant was only propagated and maintained vegetatively through cuttings.

The self-incompatible immune *S. peruvianum* source plant was crossed with a *Solanum lycopersicum* line. Embryo rescue was performed to obtain F1 offspring of this interspecific cross. The F1 was screened for resistance to Pepino Mosaic Virus, but the population was found to be susceptible.

The F1 was again self-incompatible, and intercrossing of various F1 plants was carried out to obtain an F2 population that could be used for further development.

A large number of F2 plants was tested for PepMV resistance in replicate, by making 10 cuttings of each plant to obtain identical genotypes. The PepMV resistance test identified only two highly resistant F2 plants. The level of the resistance in those plants however was still lower than the level of the original *S. peruvianum* source.

To get closer to a cultivated tomato type, the highly resistant plants were backcrossed with the *Solanum lycopersicum* line, and again embryo rescue was performed to obtain a BC1 population. The BC1's were selfed and from these around 15 BC1S1 populations were obtained. From each population between 75 and 150 plants were screened for plants that were highly resistant to PepMV, as described in Example 2.

Seven BC1S1 plants were finally selected for a good level of resistance and a BC2 was made on these plants. Embryo rescue had to be performed to obtain this BC2 generation. The BC2 was selfed again and 166 BC2S1 families were derived from this for further screening and selection. From each of those families, 150 plants were screened for resistance. Each screen consists of two steps, as described in Example 2. When a family was considered to contain a good number of resistant plants, the screen had to be repeated again with a stronger, less diluted, inoculum. In this way the highest resistance may be identified.

After each backcrossing and selfing step, a bio-assay was performed to identify highly resistant plants and to confirm the high level of resistance.

During the first generations, the PepMV resistance proved to be strongly linked to dwarf growth of the plants. This side-effect appeared to be a result of linkage drag from the resistant source. Since dwarf growth is a clearly negative characteristic, this linkage drag made the resistance not applicable for direct use in breeding. It also made it difficult to perform the bio-assays, since the plants appeared to be weak which made it challenging to keep them for a prolonged period of time. Obtaining seeds from the selected dwarf plants proved to be an even further complication.

In addition, it became apparent that the genetic constitution of the resistance was very complex. Even though the search for resistance to PepMV in tomato has been going on for a long time, no mention of cultivated *S. lycopersicum* plants with a high level of resistance to the virus had been given so far. The question of the feasibility of incorporating a high resistance level in cultivated tomato to this widespread virus therefore still had to be answered. The complexity of the genetic background of the resistance in combination with a difficult bio-assay made it very hard to identify desired progeny plants that contained the essential high level of resistance or immunity for *Solanum lycopersicum*.

QTL mapping, as described in Example 3, was therefore performed to first clarify the genetic makeup of the resistance. Marker assisted backcrossing and selection was subsequently done starting from a BC2 generation, in combination with the phenotypic screening, to detect plants that would lead to the required high level of resistance. The dwarf growth was defined to be linked to the QTL on chromosome 6, QTL1.

By using the markers for 3 QTLs, in BC2S1 two families could be developed that had a sufficiently high level of resistance, each containing two of the QTLs homozygously, and that had no more linkage drag on chromosome 6 that would result in dwarf growth. Seeds from these lines were deposited as NCIMB 41927 and NCIMB 41928.

Further backcrossing, screening and selecting as described above resulted in advanced BC4S1 populations. From one of those populations another plant which may comprise 2 QTLs, namely QTL1 and QTL2, homozygously was selected and deposited as NCIMB 42068.

The BC4S1 populations further comprised *S. lycopersicum* plants with a high level of resistance or immunity, having QTL1 and QTL2 and QTL3 homozygously. Progeny of these plants which may comprise all three QTLs homozygously was deposited as NCIMB 42069.

Example 2

Bio-Assay for Pepino Mosaic Virus Resistance

Pepino Mosaic Virus includes very aggressive genotypes, but its behaviour and symptom exhibition may be unpredictable. It is therefore extremely important for the development of resistant plants to perform a very thorough assay with sufficient repetitions to ensure a good performance in growers' conditions.

From the plants to be tested, several cuttings are made to do the assay on several plants of the same genotype. This approach prevents the selection of 'escapes', i.e. plants that are for some reason identified as being resistant, but this presumed resistance is just due to the circumstances and not because the plants contain a genetic determinant that leads to resistance. The repetitions for determining the resistance in the most optimal way are therefore formed by cuttings that together form a population of identical genotypes, which makes the results of the bio-assay highly reliable.

Inoculum for performing a bio-assay is obtained from infected tomato leaves. The bio-assay is started with an inoculum having a relatively low virus titer, in which the inoculum is for example diluted 300 times. Mechanical inoculation is than done by a standard method as is known in the art. The plants that show phenotypic resistance to PepMV at this level are selected. They comprise a genetic determinant which may comprise one or more QTLs that lead to PepMV resistance.

Plants with phenotypic resistance are preferably plants that do not show any PepMV symptoms in the bio-assay. Symptoms of the vegetative plant parts may vary and comprise 'nettle heads' (grayish, spiky plant tops), stunted heads, distorted leaves, chlorotic leaves, mosaic, mottling, or leaf spots. Screened plants may also show a reduced susceptibility as compared to a susceptible control that is included in the bio-assay, and those plants are considered to have a certain level of resistance. Susceptible controls may for example be chosen from any of the tomato varieties that are known in the art so far. Plants that show a reduced susceptibility, but which are not resistant or highly resistant or immune, do not comprise QTL1 and QTL2 and QTL3 homozygously.

Once more cuttings are made from the selected plants that preferably have a high level of resistance and did not show symptoms, to start again with a young plant stage. In this way there are again identical genotypes that are used as repetitions for obtaining the most reliable bio-assay. The selected plants are re-inoculated with an inoculum having a high virus titer, for which the inoculum is for example diluted 30 times. In this way, the strongest plants containing the best genetic determinant leading to PepMV resistance are identified. The highest level of resistance or immunity is preferably reached by the presence of QTL1 and QTL2 and QTL3 homozygously.

As an essential part of the extensive bio-assay, an ELISA assay is performed to determine that the selected plants are not just symptomless, but that the virus is also not multiplied in the plants. Accumulation of the virus will ultimately result in symptoms or weakening of a plant, and therefore such plants are not useful as durable resistant sources. It is therefore essential to confirm that the selected plants are truly free of the virus through an ELISA assay. Performing an ELISA assay to determine virus presence is a standard method known to the skilled person.

Plants with a score <0.1, which have an absorption lower than 0.1 in the ELISA test, are confirmed as resistant plants of the invention. These plants have an absorption similar to non-inoculated controls. Plants with an absorption lower than 0.1 using an inoculum of a high concentration, which has for example been 30 times diluted, which is an absorption similar to non-inoculated controls, have a resistance mechanism that is characterised as highly resistant or immunity.

Resistant plants with an absorption lower than 0.1 in the ELISA test when a lower concentrated inoculum was used, for example a 300 times diluted inoculum, are selected and backcrossed to start the next cycle. Symptom observation and ELISA testing using various inoculum concentrations is continued during the growing period, to ensure that the plants have a durable resistance.

Under many conditions no virus symptoms are visible during the bio-assay in the young plants. In these cases the ELISA assay is the only basis for the selection at this stage of plants that have a reduced susceptibility, or that are resistant, or highly resistant, or immune. An ELISA assay is preferably performed at least 14 days or at least 18 days or at least 21 days after inoculation of the cuttings, or optionally after a longer period of time during the growing period of the tomato plant.

Due to the nature of the Pepino Mosaic Virus and the complexity of the resistance, the concentration of the inoculum that is optimal to use in a bio-assay may vary. The optimal concentration varies according to the strength and concentration of the virus that is present in the plant which is used as the source for obtaining the inoculum. The optimum concentration also depends on the number of QTLs that is present in the plants to be tested. For example for the selection of plants with only one or two of the QTLs of the invention, a lower concentration of the inoculum should be used. Dilution of the inoculum for inoculation may be 3 times, 30 times, 300 times, 3000 times, 30,000 times, or any other concentration that is found to be suitable for the conditions under which the bio-assay is performed. The concentration is suitable when a clear difference in virus titer between the susceptible control and the resistant plants may be determined in an ELISA assay.

It is essential that resistant and susceptible control plants are always included as references to check if the used inoculum concentration is appropriate to use in a bio-assay. The essence of the reliability of the PepMV bio-assay lies in the inclusion of at least two different inoculum concentrations subsequently, whereby the second inoculum has the higher concentration; in the use of a number of identical genotypes, preferably through cuttings, for confirmation of the presence of resistance; and in the confirmation of a reduction of the virus or the absence of the virus or of an absorption similar to non-inoculated control plants through an ELISA assay to select plants that have reduced susceptibility or resistance or high resistance or immunity.

TABLE 1

Segregation for PepMV resistance of various BC2S1 families using a 300 times inoculum dilution

| | # of plants with absorption: | | | | | |
|---|---|---|---|---|---|---|
| BC2S1 family | <0.1 | >0.1 & <1.0 | >1.0 | NA | total | % R |
| 6278-8 | 22 | 3 | 120 | 5 | 150 | 14.7 |
| 6277-2 | 34 | 2 | 105 | 0 | 141 | 24.1 |
| 6277-3 | 60 | 2 | 79 | 0 | 141 | 42.6 |
| 6277-16 | 28 | 8 | 106 | 0 | 142 | 19.7 |
| 6277-25 | 35 | 1 | 103 | 3 | 142 | 24.6 |

TABLE 1-continued

Segregation for PepMV resistance of various BC2S1 families using a 300 times inoculum dilution

| | # of plants with absorption: | | | | | |
|---|---|---|---|---|---|---|
| BC2S1 family | <0.1 | >0.1 & <1.0 | >1.0 | NA | total | % R |
| 6278-3 | 39 | 18 | 89 | 4 | 150 | 26.0 |
| 6282-3 | 27 | 1 | 109 | 0 | 137 | 19.7 |
| 6282-4 | 28 | 1 | 107 | 1 | 137 | 20.4 |
| 6282-10 | 24 | 1 | 109 | 1 | 135 | 17.8 |
| 6282-11 | 20 | 0 | 114 | 1 | 135 | 14.8 |
| 6284-7 | 23 | 4 | 104 | 0 | 131 | 17.6 |
| 6284-12 | 54 | 5 | 87 | 2 | 148 | 36.5 |

From the table it follows that the shown BC2S1 families segregate for resistant (<0.1) and susceptible plants (>1.0). None of the BC2S1 families at this stage have all three QTLs homozygously, so segregation of the resistance is still observed. The strongest plants at this stage are selected, and subsequently inoculated with a 30 times diluted inoculum. At this stage however no plants were present having all three QTLs homozygously. Even though resistant plants were identified in the bio-assay, consequently none of them at this stage was confirmed to be highly resistant or immune after the confirmation with ELISA.

After further advancement BC4S1 *S. lycopersicum* plants could be developed that comprised QTL1 and QTL2 and QTL3 homozygously. These tomato plants were highly resistant or immune in the bio-assay for PepMV resistance. These plants further had an absorption lower than 0.1, similar to a non-inoculated control, in an ELISA test.

Example 3

QTL Mapping and Marker Development

A large population consisting of 184 BC1S1 plants as obtained from Example 1 were used for mapping the resistance to Pepino Mosaic Virus. In a first round 880 SNP markers were analysed, and an additional 559 SNP markers were included in a second round. 281 of these SNP markers were polymorphic in the first round, and in the second round 387 polymorphic SNPs could be added, resulting in a total of 671 markers that were used to do a QTL analysis for the PepMV resistance on the 184 BC plants.

Remarkably, 3 QTLs that contributed to the resistance were located, positioned on 3 separate chromosomes. Molecular SNP markers that correlated most closely to the QTLs are presented in Table 2.

For positioning the QTLs, the publicly available map SL2.40 of the *Solanum lycopersicum* genome was used as reference for all positions mentioned herein.

A first QTL which explained 8.8% of the variation was located on chromosome 6, having a LOD score of 5.34. The position of the QTL was determined to be between the physical positions 32,363,349 bp and 34,505,939 bp, preferably between positions 33,558,627 bp and 34,505,939 bp. In the BC1S1 population and subsequent progeny this QTL was linked most closely to a SNP marker on position 34,456,931, the sequence of which is found in Table 2 as SEQ ID NO:1. The borders of the preferred QTL region were identified by the presence of SEQ ID NO:4 and SEQ ID NO:5.

A second QTL, explaining 12.1% of the variation and having a LOD score of 7.12 was identified to be located on chromosome 7, between physical positions 60,667,821 bp and 62,460,220 bp, preferably between positions 61,387,356 bp and 62,253,846 bp. In the BC1S1 population and subsequent progeny developed from this population QTL2 was linked to a SNP on position 61,550,890. The sequence of the molecular SNP marker is found in Table 2 as SEQ ID NO:2. The borders of the preferred QTL region were identified by the presence of SEQ ID NO:6 and SEQ ID NO:7.

A third QTL explained 19.7% of the variation. The LOD score for this QTL was 11.03. QTL3 is located on chromosome 9 between the physical positions 60,998,420 bp and 62,512,587 bp, preferably between positions 61,494,664 bp and 62,385,023 bp, more preferably between positions 61,723,339 and 62,385,023. QTL3 is linked to a molecular SNP marker on position 61,603,006 in the BC1S1 and subsequent progeny. The sequence is found in Table 2. QTL3 is further defined by the presence of SNP markers SEQ ID NO:8 and SEQ ID NO:9.

SEQ ID NO:1 comprises the presence of a SNP from nucleotide A (wild type) to G at position 34,456,931 on the forward strand of chromosome 6. The position can also be indicated as the $16^{th}$ position (bold) in the nucleotide sequence shown in Table 2.

SEQ ID NO:2 comprises the presence of a SNP from nucleotide C (wild type) to G at position 61,550,890 on the forward strand of chromosome 7. The position can also be indicated as the $16^{th}$ position (bold) in the nucleotide sequence shown in Table 2.

SEQ ID NO:3 comprises the presence of a SNP from nucleotide C (wild type) to T at position 61,603,006 on the forward strand of chromosome 9. The position can also be indicated as the $16^{th}$ position (bold) in the nucleotide sequence shown in Table 2.

SEQ ID NO:4 comprises the presence of a SNP from nucleotide T (wild type) to C at position 33,558,627 on the forward strand of chromosome 6. The position can also be indicated as the $16^{th}$ position (bold) in the nucleotide sequence shown in Table 2.

SEQ ID NO:5 comprises the presence of a SNP from nucleotide C (wild type) to T at position 34,505,939 on the forward strand of chromosome 6. The position can also be indicated as the $16^{th}$ position (bold) in the nucleotide sequence shown in Table 2.

SEQ ID NO:6 comprises the presence of a SNP from nucleotide T (wild type) to C at position 61,387,356 on the forward strand of chromosome 7. The position can also be indicated as the $16^{st}$ position (bold) in the nucleotide sequence shown in Table 2.

SEQ ID NO:7 comprises the presence of a SNP from nucleotide C (wild type) to A at position 62,253,846 on the forward strand of chromosome 7. The position can also be indicated as the $16^{st}$ position (bold) in the nucleotide sequence shown in Table 2.

SEQ ID NO:8 comprises the presence of a SNP from nucleotide C (wild type) to T at position 61,872,648 on the forward strand of chromosome 9. The position can also be indicated as the $16^{th}$ position (bold) in the nucleotide sequence shown in Table 2.

SEQ ID NO:9 comprises the presence of a SNP from nucleotide G (wild type) to C at position 62,191,735 on the forward strand of chromosome 9. The position can also be indicated as the $16^{th}$ position (bold) in the nucleotide sequence shown in Table 2.

TABLE 2

Molecular SNP markers based on the public SL2.40 map, that in deposit numbers NCIMB 41927, NCIMB 41928, NCIMB 42068, and NCIMB 42069 are linked to QTL1, QTL2, and QTL3, which QTLs confer PepMV resistance in *Solanum lycopersicum*.

| | SNP Sequence | Indicative of |
|---|---|---|
| SEQ ID NO: 1 | GATGATCCCCCAATGGTCAAGAAATCTTGCA | QTL1 |
| SEQ ID NO: 2 | CACTGGTGAAAAAGTGGCAATTAAAAAAATT | QTL2 |
| SEQ ID NO: 3 | CTCTCAAGTTCCAGATACCGCTTCTGAGGGA | QTL3 |
| SEQ ID NO: 4 | TCTCGTTCGTGTTCTCGTCTCCTCTAATCTC | QTL1 |
| SEQ ID NO: 5 | GGACATTGAGCAGATTTCTTACTGGCTTCTG | QTL1 |
| SEQ ID NO: 6 | AGGATATGCAGCGGACGGGTTCCAAGGGCTT | QTL2 |
| SEQ ID NO: 7 | CTGAATGGAGAAGGAAGGCCTGCCAGTGTTG | QTL2 |
| SEQ ID NO: 8 | TCTTTCTTGGCTGTTTAACTCGCGATGAACG | QTL3 |
| SEQ ID NO: 9 | AAGAAAGGTTTTGGTCTTTCGCAAAAGGCAG | QTL3 |

The SNP sequences are linked to the respective QTLs in NCIMB 41927 (QTL1 and QTL2), NCIMB 42068 (QTL 1 and QTL2), NCIMB 41928 (QTL2 and QTL3), NCIMB 42069 (QTL1 and QTL2 and QTL3). The SNP sequences may be used as molecular markers for PepMV resistance in plants of said deposits.

Example 4

Transfer of the Resistance

A selfed plant from T 12R.107, still containing QTL1 and QTL2 and QTL3 homozygously, was crossed with a tomato plant that did not carry any of the resistance-conferring QTLs of the invention. The F1 obtained from the cross had all three QTLs of the invention in heterozygous state. The F1 population was not phenotypically tested for PepMV resistance, since no sufficient resistance level was expected, and additionally selection in the F1 is not relevant for this trait, since the heterozygous QTLs would all segregate in the next F2 generation.

The F1 was selfed and 250 F2 seeds were sown. Theoretically 1 out of 64 plants is expected to have all three QTLs of the invention homozygously. In the seedling stage a marker analysis was carried out, using all nine SNP markers that are mentioned in Table 2. The use of all nine markers was done to verify that potential recombinants between the resistance gene and the markers would not be selected at this stage.

Fortunately from the F2 seedlings three plants could be identified through the marker analysis that contained QTL1 and QTL2 and QTL3 homozygously, which plants were selected and kept for further breeding.

To confirm the resistance of the selected plants, cuttings were made and a bio-assay following Example 2 was performed. No symptoms were observed after the first inoculation round, using a 3000 times diluted inoculum. In the second round the inoculum was diluted 300 times, and again no Pepino Mosaic Virus symptoms were found. As the susceptible control the hybrid variety Mecano was used, which showed clear leaf symptoms in early plant stage.

To make sure that the virus had not accumulated in the selected plants, and again following the assay described in Example 2, an ELISA test was done on the selected plants after symptoms had occurred on the susceptible control in the second inoculation round. The ELISA assay showed an absorption comparable to the immune source, and therefore confirmed that virus accumulation in the selected plants was negligible. During the growing period of the plants, including during fruit set, ELISA assays were performed repeatedly to make sure that the plants would also stay resistant during the generative stage.

The invention is further described by the following numbered paragraphs:

1. Tomato plant (*Solanum lycopersicum* L.) carrying a genetic determinant that comprises one or more of QTL1, QTL2 and QTL3, which genetic determinant confers resistance to Pepino Mosaic Virus, and which QTLs are as comprised in tomato plants representative seed of which were deposited with the NCIMB under deposit numbers NCIMB 41927, NCIMB 41928, NCIMB 42068, and NCIMB 42069.

2. Tomato plant (*Solanum lycopersicum* L.) comprising a genetic determinant that confers resistance to Pepino Mosaic Virus (PepMV), wherein the genetic determinant comprises:
   QTL1, located on Linkage Group (LG) 6 between the physical positions 32,363,349 bp and 34,505,939 bp, preferably between positions 33,558,627 bp and 34,505,939 bp, or a PepMV-resistance-conferring part thereof, and/or
   QTL2, located on Linkage Group (LG) 7 between the physical positions 60,667,821 bp and 62,460,220 bp, preferably between positions 61,387,356 bp and 62,253,846 bp, or a PepMV-resistance-conferring part thereof, and/or
   QTL3, located on Linkage Group (LG) 9 between the physical positions 60,998,420 bp and 62,512,587 bp, preferably between positions 61,494,664 bp and 62,385,023, more preferably between positions 61,723,339 bp and 62,385,023 bp, or a PepMV-resistance-conferring part thereof.

3. Tomato plant of paragraph 1 or 2, wherein the genetic determinant comprises:
   QTL1 or a PepMV-resistance-conferring part thereof and QTL2 or a PepMV-resistance-conferring part thereof, or
   QTL1 or a PepMV-resistance-conferring part thereof and QTL3 or a PepMV-resistance-conferring part thereof, or
   QTL2 or a PepMV-resistance-conferring-part thereof and QTL3 or a PepMV resistance-conferring part thereof.

4. Tomato plant of any of paragraphs 1-3, wherein the genetic determinant comprises QTL1 or a PepMV-resistance-conferring part thereof, and QTL2 or a PepMV-resistance-conferring part thereof, and QTL3 or a PepMV-resistance-conferring part thereof.

5. Tomato plant of any of paragraphs 1-4, obtainable by a method comprising:
   a) crossing a plant comprising QTL1 and QTL2, representative seed of which was deposited as NCIMB 41927 or NCIMB 42068, or a plant comprising QTL2 and QTL3, representative seed of which was deposited as NCIMB 41928, or a plant comprising QTL1 and QTL2 and QTL3 representative seed of which was deposited as NCIMB 42069 with a plant not comprising the genetic determinant to obtain an F1 population;
   b) performing one or more rounds of selfing and/or crossing a plant from the F1 to obtain a further generation population;
   c) optionally selecting a plant from the population that comprises one or two of the QTLs 1, 2 and 3, followed by crossing with a plant comprising at least the other QTLs of QTL 1, 2 and 3, and subsequently repeating step b);
   d) selecting a plant that comprises QTL1 and QTL2 and QTL3.

6. Tomato plant of any of paragraphs 1-4, obtainable by crossing a first parent plant that comprises QTL1 and/or QTL2 and/or QTL3 with a second parent plant that comprises QTL1 and/or QTL2 and/or QTL3 and selecting in subsequent generations, optionally after further selfing and/or crossing steps, for a plant that comprises QTL1 and QTL2, or QTL 1 and QTL3, or QTL2 and QTL3, or QTL1 and QTL2 and QTL3.

7. Seed of a tomato plant of any one of paragraphs 1-6, wherein the plant that can be grown from the seed comprises one or more of the QTLs 1-3 as defined in paragraph 2.

8. Seed of paragraph 7, wherein the plant that can be grown from the seed is resistant to Pepino Mosaic Virus.

9. Progeny of a tomato plant of any one of paragraphs 1-6 or of tomato seed of paragraph 7 or 8, comprising one or more of the QTLs 1-3 as defined in paragraph 2.

10. Progeny of paragraph 9, which is resistant to Pepino Mosaic Virus.

11. Propagation material suitable for producing a plant of any one of paragraphs 1-6, 9 and 10 or for producing seed of paragraph 7 or 8, wherein the propagation material is suitable for sexual reproduction, and is in particular selected from microspores, pollen, ovaries, ovules, embryo sacs and egg cells, or is suitable for vegetative reproduction, and is in particular selected from cuttings, roots, stems, cells, protoplasts, or is suitable for tissue cultures of regenerable cells, and is in particular selected from leaves, pollen, embryos, cotyledon, hypocotyls, meristematic cells, roots, root tips, anthers, flowers, seeds and stems, wherein a plant produced from the propagation material comprises one or more of the QTLs 1-3 as defined in paragraph 2.

12. Propagation material of paragraph 11, wherein the plant produced from the propagation material is resistant to Pepino Mosaic Virus.

13. Tomato plant of any of paragraphs 1 to 6, 9 and 10, seeds of paragraph 7 or 8 or propagation material of paragraph 11 or 12, comprising:
   QTL1 or a resistance conferring part thereof, which in deposit NCIMB 41927 and/or NCIMB 42068 and/or NCIMB 42069 is linked to molecular markers characterized by SEQ. ID No. 1, SEQ. ID No. 4 and SEQ ID NO:5 and/or QTL2 or a resistance conferring part thereof, which in deposits NCIMB 41927 and/or NCIMB 41928 and/or NCIMB 42068 and/or NCIMB 42069 is linked to molecular markers characterized by SEQ. ID No. 2, SEQ ID NO:6 and SEQ ID NO:7, and/or QTL3 or a resistance conferring part thereof, which in deposit NCIMB 41928 and/or NCIMB 42069 is linked to molecular markers characterized by SEQ. ID No. 3, SEQ ID NO:8 and SEQ ID NO:9.

14. A tomato fruit of a plant of any one of paragraphs 1-6, 9, 10 or 13.

15. Food product, comprising the tomato fruit of paragraph 14, or parts thereof, optionally in processed form.

16. Use of a plant of any one of paragraphs 1 to 6, 9, 10 or 13, or plants produced from the seeds of paragraph 7 or 8, or from the propagation materials of paragraph 11 or 12 as germplasm in a breeding programme for the development of Pepino Mosaic Virus resistant tomato plants.

17. Molecular marker, preferably a molecular SNP marker, present in a *Solanum* lycopersicum genome, which molecular marker is genetically linked to a QTL that confers resistance to Pepino Mosaic Virus in *Solanum lycopersicum*, and which molecular marker is characterised by any of the SEQ ID NOs:1-9 and wherein the QTL is preferably as defined in paragraph 2.

18. Use of a marker of paragraph 17 for identifying a Pepino Mosaic Virus resistance conferring QTL in a *Solanum lycopersicum* plant.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A *Solanum lycopersicum* L. tomato plant carrying a genetic determinant that comprises
   QTL1, linked to molecular markers characterized by SEQ ID NOs. 1, 4 and 5; and
   QTL2, linked to molecular markers characterized by SEQ ID NOs. 2, 6 and 7; and
   QTL3, linked to molecular markers characterized by SEQ ID NOs. 3, 8 and 9;
   wherein the genetic determinant confers resistance to Pepino Mosaic Virus, and said QTLs are as comprised in a tomato plant, representative seeds of which were deposited with the NCIMB under deposit number NCIMB 42069.

2. The *Solanum lycopersicum* L. tomato plant as claimed in claim 1, wherein:
   QTL1 is located on Linkage Group (LG) 6 between the physical positions 33,558,627 by and 34,505,939 bp, and
   QTL2 is located on Linkage Group (LG) 7 between the physical positions 61,387,356 by and 62,253,846 bp, and
   QTL3 is located on Linkage Group (LG) 9 between the physical positions 61,494,664 by and 62,385,023 bp.

3. The tomato plant as claimed in claim 1, obtained by a method comprising:
   a) crossing a plant comprising QTL1 and QTL2, representative seed of which was deposited as NCIMB 41927 or NCIMB 42068, or a plant comprising QTL2 and QTL3, representative seed of which was deposited as NCIMB 41928, or a plant comprising QTL1 and QTL2 and QTL3 representative seed of which was deposited as NCIMB 42069 with a plant not comprising the genetic determinant to obtain an F1 population;
   b) performing one or more rounds of selfing and crossing a plant from the F 1 to obtain a further generation population;
   c) optionally selecting a plant from the population that comprises one or two of the QTLs 1, 2 and 3, followed by crossing with a plant comprising at least the other QTLs of QTL 1, 2 and 3, and subsequently repeating step b); and
   d) selecting a plant that comprises QTL1 and QTL2 and QTL3.

4. A seed of the tomato plant as claimed in claim 1, wherein the plant that is grown from the seed comprises:
   QTL1, linked to molecular markers characterized by SEQ ID NOs. 1, 4 and 5; and
   QTL2, linked to molecular markers characterized by SEQ ID NOs. 2, 6 and 7; and
   QTL3, linked to molecular markers characterized by SEQ ID NOs. 3, 8 and 9;.

5. The seed as claimed in claim 4, wherein the plant that is grown from the seed is resistant to Pepino Mosaic Virus.

6. A progeny of the tomato plant as claimed in claim 1, comprising:
   QTL1, linked to molecular markers characterized by SEQ ID NOs. 1, 4 and 5; and
   QTL2, linked to molecular markers characterized by SEQ ID NOs. 2, 6 and 7; and
   QTL3, linked to molecular markers characterized by SEQ ID NOs. 3, 8 and 9;.

7. The progeny as claimed in claim 6, which is resistant to Pepino Mosaic Virus.

8. A propagation material suitable for producing the plant as claimed in claim 1, wherein the propagation material is suitable for sexual reproduction, and is selected from microspores, pollen, ovaries, ovules, embryo sacs and egg cells, or is suitable for vegetative reproduction, and is selected from cuttings, roots, stems, cells, protoplasts, or is suitable for tissue cultures of regenerable cells, and is selected from leaves, pollen, embryos, cotyledon, hypocotyls, meristematic cells, roots, root tips, anthers, flowers, seeds and stems, wherein a plant produced from the propagation material comprises:
   QTL1, linked to molecular markers characterized by SEQ ID NOs. 1, 4 and 5; and
   QTL2, linked to molecular markers characterized by SEQ ID NOs. 2, 6 and 7; and
   QTL3, linked to molecular markers characterized by SEQ ID NOs. 3, 8 and 9;.

9. The propagation material as claimed in claim 8, wherein the plant produced from the propagation material is resistant to Pepino Mosaic Virus.

10. A tomato fruit of the plant as claimed in claim 1.

11. A propagation material suitable for producing the seed as claimed in claim 4,
    wherein the propagation material is suitable for sexual reproduction,
    wherein the propagation material comprises a microspore, pollen, ovary, ovule, embryo sac or egg cell, and
    wherein a plant produced from the propagation material comprises:
      QTL1, linked to molecular markers characterized by SEQ ID NOs. 1, 4 and 5; and
      QTL2, linked to molecular markers characterized by SEQ ID NOs. 2, 6 and 7; and
      QTL3, linked to molecular markers characterized by SEQ ID NOs. 3, 8 and 9;.

12. The propagation material as claimed in claim 11, wherein the plant produced from the propagation material is resistant to Pepino Mosaic Virus.

13. A propagation material suitable for producing seed as claimed in claim 4, wherein the propagation material is suitable for vegetative reproduction,
    wherein the propagation material comprises a cutting, root, stem, cell or protoplast, and
    wherein a plant produced from the propagation material comprises:
      QTL1, linked to molecular markers characterized by SEQ ID NOs. 1, 4 and 5; and
      QTL2, linked to molecular markers characterized by SEQ ID NOs. 2, 6 and 7; and QTL3, linked to molecular markers characterized by SEQ ID NOs. 3, 8 and 9;.

14. A propagation material suitable for producing seed as claimed in claim 4, wherein the propagation material is suitable for tissue cultures of regenerable cells,
  wherein the propagation material comprises a leaf, pollen, embryo, cotyledon, hypocotyl, meristematic cell, root, root tip, anther, flower, seed or stem, and
  wherein a plant produced from the propagation material comprises:
    QTL1, linked to molecular markers characterized by SEQ ID NOs. 1, 4 and 5; and
    QTL2, linked to molecular markers characterized by SEQ ID NOs. 2, 6 and 7; and
    QTL3, linked to molecular markers characterized by SEQ ID NOs. 3, 8 and 9;.

* * * * *

UNITED STATES PATENT AND TRADEMARK OFFICE
CERTIFICATE OF CORRECTION

PATENT NO. : 9,637,757 B2  
APPLICATION NO. : 13/774665  
DATED : May 2, 2017  
INVENTOR(S) : Arie Vogelaar et al.

Page 1 of 1

It is certified that error appears in the above-identified patent and that said Letters Patent is hereby corrected as shown below:

In the Claims

At Column 29, Line 28, (Claim 2), please change: "physical positions 33,558,627 by and 34,505,939 bp," to: --physical positions 33,558,627 bp and 34,505,939 bp,--

At Column 29, Line 31, (Claim 2), please change: "physical positions 61,387,356 by and 62,253,846 bp," to: --physical positions 61,387,356 bp and 62,253,846 bp,--

At Column 29, Line 34, (Claim 2), please change: "physical positions 61,494,664 by and 62,385,023 bp." to: --physical positions 61,494,664 bp and 62,385,023 bp.--

At Column 29, Line 63, (Claim 4), please change: "ID NOs. 3, 8 and 9;." to: --ID NOs. 3, 8 and 9.--

At Column 30, Line 15, (Claim 6), please change: "ID NOs. 3, 8 and 9;." to: --ID NOs. 3, 8 and 9.--

At Column 30, Line 35, (Claim 8), please change: "ID NOs. 3, 8 and 9;." to: --ID NOs. 3, 8 and 9.--

At Column 30, Line 53, (Claim 11), please change: "SEQ ID NOs. 3, 8 and 9;." to: --SEQ ID NOs. 3, 8 and 9.--

At Column 31, Line 2, (Claim 13), please change: "SEQ ID NOs. 3, 8 and 9;." to: --SEQ ID NOs. 3, 8 and 9.--

At Column 31, Line 16, (Claim 14), please change: "SEQ ID NOs. 3, 8 and 9;." to: --SEQ ID NOs. 3, 8 and 9.--

Signed and Sealed this  
Sixth Day of June, 2017

Michelle K. Lee  
*Director of the United States Patent and Trademark Office*